(12) United States Patent
Chornenky et al.

(10) Patent No.: US 6,473,491 B2
(45) Date of Patent: *Oct. 29, 2002

(54) METHOD AND X-RAY DEVICE USING ADAPTABLE POWER SOURCE

(75) Inventors: Victor I. Chornenky, Minnetonka; Graham S. Kerslick, Minneapolis; Michael R. Satteson; Steven T. Meyer, both of St. Paul, all of MN (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/748,296

(22) Filed: Dec. 21, 2000

(65) Prior Publication Data

US 2001/0016031 A1 Aug. 23, 2001

Related U.S. Application Data

(63) Continuation of application No. 09/262,149, filed on Mar. 3, 1999, now abandoned.

(51) Int. Cl.[7] .............................. H05G 1/34; A61N 5/10
(52) U.S. Cl. ......................... 378/122; 378/109; 378/65; 378/111
(58) Field of Search .......................... 378/65, 122, 109, 378/111

(56) References Cited

U.S. PATENT DOCUMENTS

| 5,090,043 A | * | 2/1992 | Parker et al. ................ 378/122 |
| 5,621,780 A | * | 4/1997 | Smith et al. .................... 378/65 |
| 5,729,583 A | * | 3/1998 | Tang et al. .................. 378/122 |
| 5,748,699 A | * | 5/1998 | Smith ........................... 378/65 |
| 6,069,938 A | * | 5/2000 | Chornenky et al. ......... 378/122 |
| 6,108,402 A | * | 8/2000 | Chornenky et al. ........... 378/65 |
| 6,148,061 A | * | 11/2000 | Shefer et al. ................ 378/122 |

* cited by examiner

Primary Examiner—Drew A. Dunn
(74) Attorney, Agent, or Firm—Catherine C. Maresh

(57) ABSTRACT

A method described includes positioning an x-ray emitter at a treatment area, where the x-ray emitter is connected to a cable, setting a voltage source at a source voltage, and measuring a current through the x-ray emitter. The method may include comparing a current flowing through the emitter with a limit and a low limit. The method further includes increasing the source voltage if the current is higher than the high limit. The method includes determining the high limit and the low limit based on the source voltage and the desired radiation. An apparatus of the invention includes an x-ray emitter with a voltage source and a current sensor. The apparatus may include a current comparison device for comparing the measured current with a high limit and a low limit, and further include a voltage source control. A current integrator for integrating a current from the x-ray emitter may also be included.

20 Claims, 2 Drawing Sheets

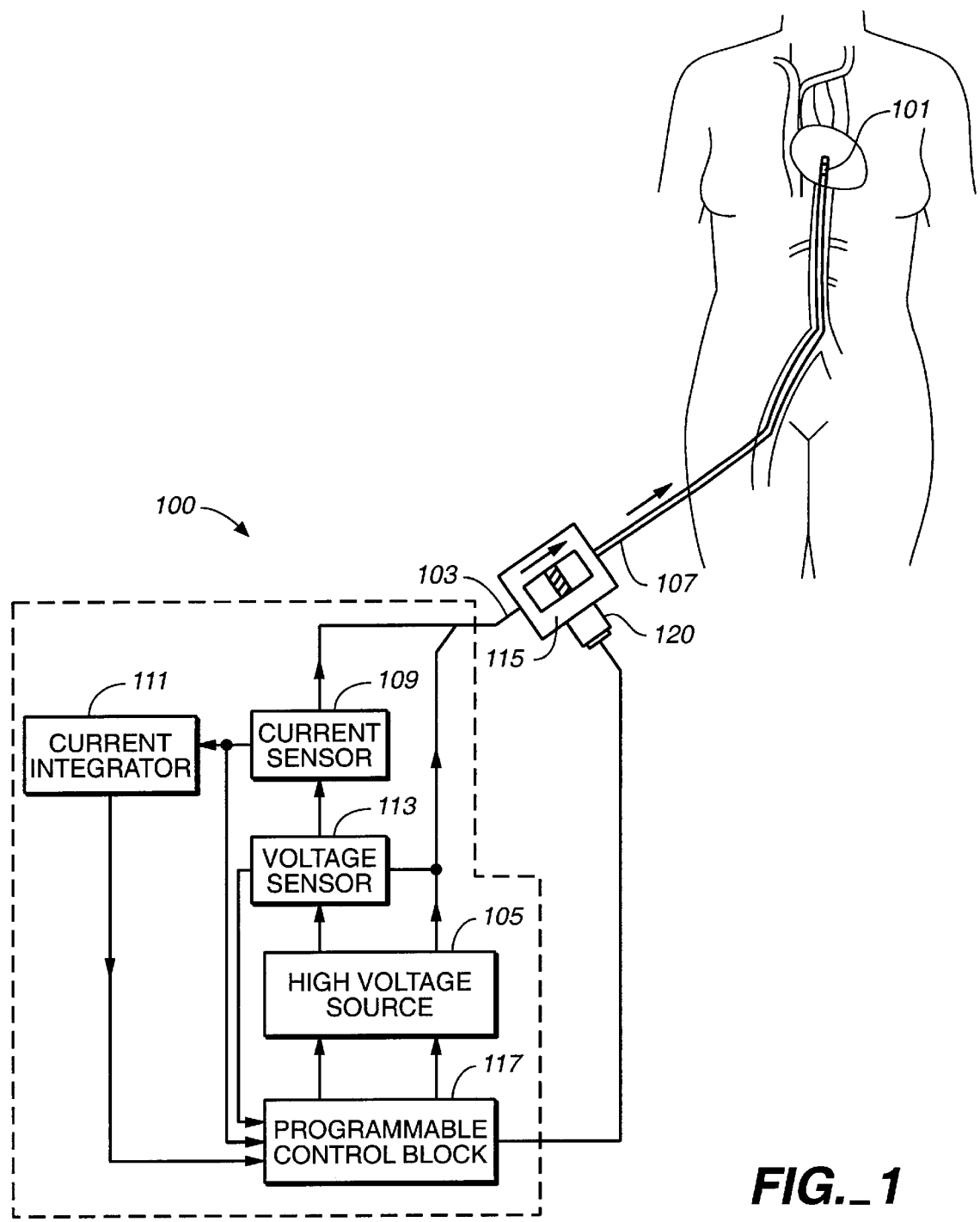
FIG._1

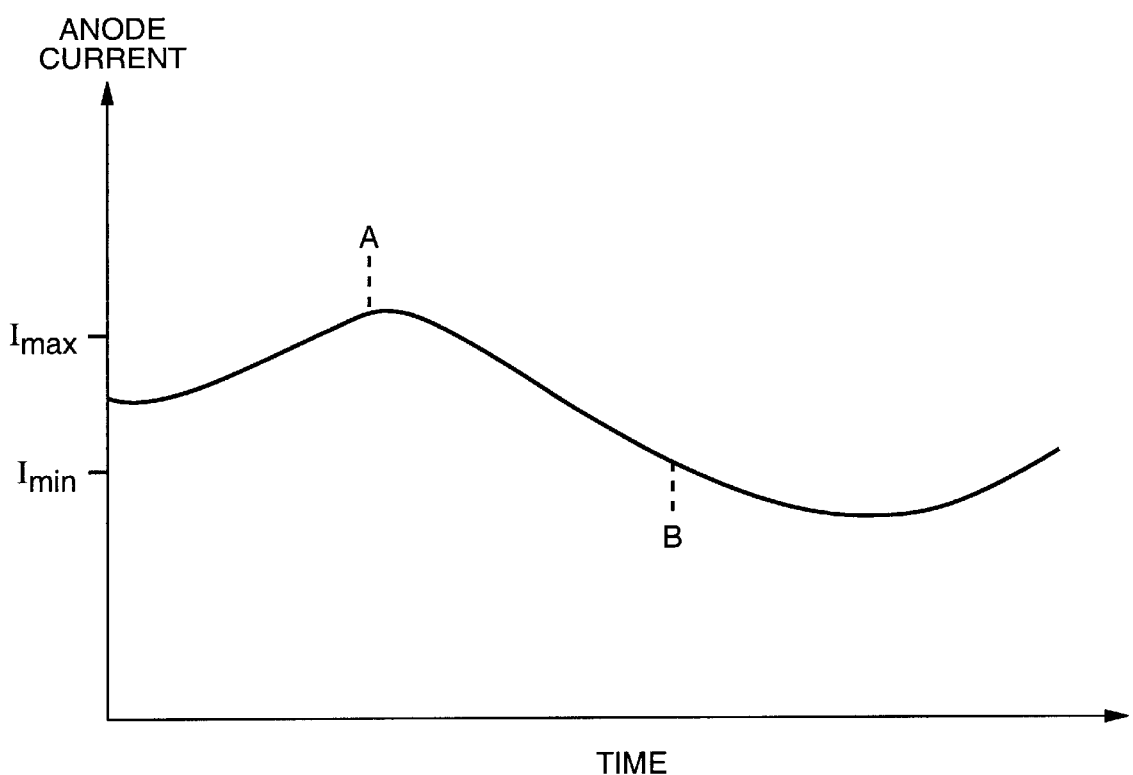
FIG._2

METHOD AND X-RAY DEVICE USING ADAPTABLE POWER SOURCE

This is a continuation of application Ser. No. 09/262,149, filed Mar. 3, 1999 now abandoned.

BACKGROUND OF THE INVENTION

The present invention relates to an apparatus and method for exposing a treatment area in a passage inside a patient to x-ray radiation. In particular, the invention relates to a method and apparatus for x-ray treatment using an adaptable voltage source to an x-ray emitter.

The x-ray catheter of this application and various delivery systems for positioning such a catheter in a passage inside the body of a patient are described in co-pending patent application Ser. No. 08/701,764, "X-RAY CATHETER", the contents of which are incorporated herein by reference.

From an electrical standpoint the x-ray emitter is a high voltage vacuum diode with a cold cathode. Typically, hot cathodes are used in standard x-ray tubes. A hot cathode has a third electrode which provides a low voltage current for heating the cathode and allows the anode current to be controlled by changing the temperature of the cathode.

In many x-ray devices, a field emission cathode, or a cold cathode, is preferred to a hot cathode. Space limitations in a very small device may eliminate the possibility of a third electrode. The desire to avoid heat generation at the x-ray emitter may also preclude the use of a hot cathode.

A disadvantage of a cold cathode diode system is that at any given stabilized voltage on the anode-cathode gap, the current is unstable in time, due to some inherent instabilities of the emission characteristics. The current can therefore run too high or too low compared with a desired current for the particular application. Too low a current will make the treatment time unacceptably long and too high a current can cause overheating of the emitter, possibly resulting in a high voltage discharge and destruction of the emitter. In addition, an unstable current makes it difficult to provide a precise accumulated dose, since the delivered dose is proportional to the current through the emitter.

A power source for an x-ray device is needed that compensates for inherent instabilities of the current over time. This type of power source is especially needed in x-ray devices having a cold cathode.

SUMMARY OF THE INVENTION

The present invention relates to an apparatus and a method for exposing a treatment area in a passage inside a patient to x-ray radiation.

The method includes positioning an x-ray emitter at a treatment area, where the x-ray emitter is connected to a cable, setting a voltage source at a source voltage, and measuring a current through the x-ray emitter.

The method may include comparing a current with a high limit and a low limit. The method further includes increasing the source voltage if the current is lower than the low limit. The method further includes decreasing the source voltage if the current is higher than the high limit. The method includes determining the high limit and the low limit based on the source voltage and the desired radiation.

An apparatus of the invention includes an x-ray emitter, positionable in the passage, a cable connected to the x-ray emitter, a voltage source connected to the cable, and a current sensor for measuring the current.

The apparatus may include a current comparison device for comparing the measured current with a high limit and a low limit, and further include a voltage source control device operatively connected to the current comparison device. The embodiment may include a current integrator for integrating a current measured at the x-ray emitter.

These and various other features of novelty which characterize the invention are pointed out with particularity in the application. However, for a better understanding of the invention, its advantages, and the objects obtained by its use, reference should be made to the accompanying drawings, claims and descriptive matter, which form a part hereof.

BRIEF DESCRIPTION OF THE DRAWINGS

FIG. 1 is a schematic overview of an embodiment of the present invention; and

FIG. 2 is a schematic diagram showing the anode current in an embodiment of the invention.

DETAILED DESCRIPTION OF THE DRAWINGS

A method for using an x-ray device having an adaptable power source is described, where the voltage source is adjusted to maintain the current at an x-ray emitter within predetermined limits. If the emitter current drops below a minimum current, the voltage supplied to the device is increased automatically. If the emitter current rises above a maximum current, the voltage supplied to the x-ray device decreases automatically.

An advantage of an embodiment of the present invention is that it allows an x-ray emitter to be operated to deliver a precise radiation dose in spite of low current stability and varying characteristics of cold cathodes. Another advantage is that the inclusion of a current integrator in the device allows the delivered dose to be determined during treatment.

Examples of the x-ray emitter of this application, components of the emitter, and various delivery systems for positioning such a catheter in a passage inside the body of a patient have been described in other co-pending patent applications. The x-ray emitter is described in patent application Ser. No. 08/701,764, "X-RAY CATHETER", the contents of which are incorporated by reference herein. Several delivery devices, systems and methods use with an x-ray emitter are described in U.S. patent application Ser. No. 09/036,602, titled "DEVICES, SYSTEMS AND METHODS OF DELIVERING X-RAY RADIATION", filed on Mar. 6, 1998, the contents of which are hereby incorporated by reference herein.

In particular, the x-ray device may comprise a sheath with a wall, the sheath having proximal and distal end and a primary lumen longitudinally through it. The sheath may be formed from many different elastomeric materials that are suitable in consideration of the intended application of the embodiment. In one application, for example, the sheath is to be advanced through a blood vessel in a patient, to position the x-ray device in the vicinity at a treatment area, The sheath may for example be formed from a polymer material using well known extrusion techniques or other processing techniques.

The x-ray catheter is introduced into a patient's body using ordinary techniques in the art. For example, where the x-ray catheter is to be introduced into a blood vessel, typically, an incision is made to the blood vessel and a vessel expander is introduced. The vessel expander provides a pathway lumen into the vessel through which other implements, such as the guidewire and the sheath, can be introduced. The x-ray emitter coupled to the cable is placed in the proximal end of the primary lumen so that the x-ray emitter is positioned at the distal end of the treatment area.

An x-ray device of the present invention includes an anode and a cathode, arranged within a vacuum housing to produce x-ray radiation. The cathode may include a thin diamond film, and may include a getter material that is activated to improve the quality of the vacuum within the housing, as described in U.S. patent application Ser. No. 08/806,244 now U.S. Pat. No. 6,377,846, that is incorporated by reference herein. The vacuum housing may include a diamond shell, as described in U.S. patent application Ser. No. 09/008,202, now U.S. Pat. No. 6,108,402, titled "A DIAMOND VACCUM HOUSING FOR MINIATURE X-RAY DEVICE", filed on Jan. 16, 1998, the entirety of which is incorporated by reference herein.

A pulse high voltage source that may be used in connection with the x-ray device of the present invention is described in co-pending U.S. patent application Ser. No. 09/067,844, now U.S. Pat. No. 6,069,938, "METHOD AND X-RAY DEVICE USING A PULSE HIGH VOLTAGE SOURCE", filed on Apr. 27, 1998 which is incorporated herein by reference in its entirety.

A schematic overview of an embodiment of the apparatus of the invention is shown FIG. 1. The apparatus 100 includes an x-ray emitter 101 connected to a cable 103. The x-ray emitter 101 is schematically shown at a position inside a patient's body. As described in detail in the above referenced patent applications, the x-ray emitter 101 and cable 103 may be inserted into the patient's body using known techniques. Where a blood vessel is to be treated, an incision, a vessel expander, and an outer sheath may be used. Then the emitter is advanced through the blood vessel to the desired treatment area. In the illustrated embodiment the sheath is denoted by reference numeral 107. The cable 103 is connected to a high voltage source 105. Different well known high voltage sources may be used in the embodiment shown in FIG. 1. The high voltage source supplies a voltage ranging between about 10 and 40 KV.

The apparatus 100 includes a current sensor 109. The current sensor 109 is connected to the cable and may be connected to the control circuit. The current sensor may be used for measuring the current through the x-ray emitter 101. Many well-known current sensors may be used with this embodiment. For example, an amperemeter may be used to measure the current. The current through an x-ray emitter at a given operational voltage may differ from emitter to emitter. Despite advanced manufacturing processes, the current and voltage characteristics will typically vary between emitters. Also, due to statistical fluctuations and changes in operating conditions, the current through an emitter at a given operational voltage may vary during the treatment. The varying current during treatment presents a problem because excessive currents can damage the x-ray emitter and potentially pose a danger to the patient and operator. Also, it is difficult to determine the delivered dose if the current varies, since the delivered dose is proportional to the accumulated current through the x-ray emitter during the treatment.

The apparatus 100 may further include a current comparison device, for comparing a measured current with a predetermined high limit and low limit. In an embodiment of the present invention the current comparison device may be a physically separate device or it may be included in the control circuit 117 and/or parts of the current sensor 109. The predetermined high and low limits may for example be entered by the operator, or be stored in the control circuit 117. The high and low limits may be determined based on the operating voltage and the desired delivery dose of radiation. The operation of the current comparison device is further illustrated by FIG. 2. The anode current is shown as a function of time. On the current axis the high limit $I_{max}$ and the low limit $I_{min}$ are indicated. If the comparison shows that the measured current is higher than the high limit, as in the point indicated by A, the current comparison device will lower the output voltage from the high voltage source 105. If the comparison shows that the measured current is lower than the low limit, as in the point indicated by B, the current comparison device will increase the output voltage from the high voltage source 105. If the comparison shows that the measured current is within the range of the high limit and the low limit, the output voltage will not be changed. It will be understood that the illustrated diagram is schematic only, and does not necessarily provide an accurate description of the quantity of anode current during operation.

The operation and configuration of the above described apparatus may be further understood by the following description of the use of the embodiment. The apparatus 100 may further include a catheter pull-back assembly 115. The catheter pull-back assembly may include a body with a carriage slidably mounted on it. The sheath 107 may be connected to the body and the cable 103 may be connected to the carriage. By sliding the carriage on the body of the catheter pull-back assembly, the cable may be retracted within the sheath 107, thereby moving the x-ray emitter 101. The catheter pull-back assembly may further include means for actuating the carriage from a distance. For example an actuating cable may be connected to the carriage so that the carriage can be actuated by a control means, such as electro motor 120 separate from the catheter pull-back assembly. The catheter movement could also be controlled by hand.

The apparatus 100 may further include a control circuit 117 connected to the high voltage source 105. The control circuit 117 may include different configurations of circuit boards, components, input and output devices, depending on the particular intended use of the invention. The control circuit 117 may for example be used to run a basic algorithm to control the components of the apparatus 100. For these purposes, the control circuit 117 may be connected to the voltage sensor 113, the current integrator 111, and the catheter pull-back assembly 115. For purposes of sharing measurements between these devices, there may be an electric or digital connection from the device to the control circuit 117. For other purposes such as controlling the movement of the x-ray emitter via the catheter pull-back assembly 115, there may be a mechanical connection, such as an actuator cable from the pull-back assembly 115 to the control circuit.

In using the embodiment of the invention, an x-ray emitter 101 is positioned in a passage inside a patient's body according to known procedures for catherization. The x-ray emitter is typically positioned near a particular treatment area that is to be treated with radiation. For example the x-ray emitter 101 may be positioned distal to the treatment area, such that it may be successively withdrawn during the treatment to deliver radiation to the entire treatment area. For example the x-ray emitter 101 may be delivered by connecting the x-ray emitter to a cable 103 and advancing the cable 103 through a sheath 107 that has been introduced in the passage. Furthermore, the sheath may be advanced in the passage using a guide wire (not shown) by first introducing the guide wire in the passage, and then advancing the sheath along the guide wire into the passage. The cable 103 is connected to the carriage of the catheter pull-back assembly 115. The sheath 107 is connected to the body of the pull-back assembly.

The particular treatment parameters for the patient may be entered into the control circuit 117. For example, the operating voltage, the length of the treatment area, and the desired delivered dose may be entered as treatment parameters. The operating voltage determines the depth of penetration. The desired delivered dose depends on the surrounding tissue and the medical condition to be treated. When the x-ray emitter is in its initial position and the treatment parameters have been entered the treatment begins. High voltage is supplied to the x-ray emitter and x-ray radiation is emitted. The measured current through the x-ray emitter is integrated by the current integrator and when the desired dose has been delivered, the control circuit will stop the supply of high voltage to the x-ray emitter.

If at any time during the x-ray treatment the current through the x-ray emitter falls below a low limit, the source voltage will be increased to produce a higher current. If at any time during the treatment the measured current through the x-ray device is higher than a high limit, the source voltage will be decreased to produce a lower current through the x-ray device. When the desired radiation dose has been delivered, the x-ray emitter may be moved in the passage inside the patient's body. After the x-ray emitter has been moved to a new position in the passage the treatment process may be repeated as described above. For example, the x-ray emitter may be moved by one or more steps, each step being between about 0.1 and 3 millimeter. When the x-ray emitter has traveled the full length of the treatment area length, the supply of high voltage to the x-ray emitter is terminated and the treatment sequence is complete. The dosage of x-ray radiation to be applied to the interior of a body will generally be within the scope of the attending physicians judgment, and will be based on individual conditions, such as the condition at the area to be treated and the particular patient. For example, in order to treat the early stages Barrett's esophagus, only the first layer of cells may need to be irradiated. If Barrett's esophagus has progressed to a cancerous state, the amount of radiation delivered will typically increase.

According to the present invention, x-ray radiation in the range of 10 to 50 Grays may be applied to an area of the interior of a passage during treatment, for example, to prevent restenosis. Preferably, x-ray radiation in the range of 15 to 30 Grays may be applied to an interior body site. The treatment will be structured to last about 2 to 10 minutes, or, more preferably, 3 to 5 minutes. The x-ray emitter may be repositioned during the course of radiation treatment, depending on the length of the area requiring treatment.

The voltage applied to the emitter affects the depth of penetration of the irradiation. Therefore, the resulting change in depth of penetration should be considered when setting the increments and limits for voltage source change.

It is to be understood, that even though numerous characteristics and advantages of the invention have been set forth in the foregoing description, together with details of the structure and function of the invention, the disclosure is illustrative only, and changes may be made in detail, especially in matters of shape, size, and arrangement of the parts within the principles of the invention to the full extent indicated by the broad general meaning of the terms in which the appended claims are expressed.

We claim:

1. A method for exposing a treatment area in a passage inside a patient to X-ray radiation, the method comprising:
   positioning a sheath in a blood vessel inside the patient;
   positioning an X-ray emitter through the sheath at the treatment area, the X-ray emitter being connected to a pullback assembly and the X-ray emitter including a field emission cathode;
   setting a voltage source at a source voltage; and
   measuring a current through the X-ray emitter.

2. The method of claim 1, further comprising comparing the current with a high limit and a low limit.

3. The method of claim 2, further comprising increasing the source voltage if the current is lower than the low limit.

4. The method of claim 2, further comprising decreasing the source voltage if the current is higher than the high limit.

5. The method of claim 2, further comprising determining the high limit and low limit based on the source voltage and a desired dose of radiation.

6. The method of claim 1, wherein positioning the X-ray emitter comprises advancing the X-ray emitter and the cable through a sheath in the passage and further comprising the steps of placing a guide wire in the passage, and advancing the sheath in the passage using the guide wire.

7. The method of claim 1, wherein setting the voltage source comprises setting the voltage source at between about 10 and 40 KV.

8. The method of claim 7, wherein setting the voltage source comprises setting the voltage source to generate rectangular voltage pulses.

9. The method of claim 1, further comprising moving the X-ray emitter past a length of the treatment area.

10. The method of claim 9, wherein moving the X-ray emitter comprises moving the X-ray emitter using the pullback assembly comprising a body with a carriage slidably mounted thereon.

11. The method of claim 9, wherein moving the X-ray emitter comprises moving the X-ray emitter by at least one step of between about 0.1 and 3 mm.

12. The method of claim 1, further comprising the step of measuring the current through the X-ray emitter with a current integrator.

13. The method of claim 12, further comprising the step of discontinuing the current through the X-ray emitter when a predetermined amount of electric charge has passed through the X-ray emitter.

14. An apparatus for exposing a treatment area in a blood vessel inside a patient to X-ray radiation, the apparatus comprising:
   A sheath;
   an X-ray emitter, the X-ray emitter including a field emission cathode, positionable in the sheath;
   a pullback assembly connected to the X-ray emitter;
   a voltage source, connected to the cable; and
   a current sensor for measuring the current, connected to the voltage source and to the cable.

15. The apparatus of claim 14, further comprising a control circuit connected to the cable, the voltage source and the current sensor.

16. The apparatus of claim 15, wherein the control circuit further comprises a current comparison device.

17. The apparatus of claim 16, wherein the control circuit further comprises a voltage source control device, operatively connected to the current comparison device.

18. The apparatus of claim 15, further comprising the pullback assembly connected to the control circuit for moving the X-ray emitter, the pullback assembly comprising a body slidably moveable on a carriage.

19. The apparatus of claim 15, further comprising a current integrator connected to the current sensor, the voltage source, and the control circuit for measuring the current from the X-ray emitter.

20. The apparatus of claim 19, wherein the control circuit comprises means for controlling the voltage source to operate such that a predetermined amount of electric charge passes through the X-ray emitter.

* * * * *